US011020272B2

(12) United States Patent
Raksi

(10) Patent No.: US 11,020,272 B2
(45) Date of Patent: Jun. 1, 2021

(54) LASER SCANNER

(71) Applicant: AMO Development, LLC, Santa Ana, CA (US)

(72) Inventor: Ferenc Raksi, Irvine, CA (US)

(73) Assignee: AMO Development, LLC, Santa Ana, CA (US)

(*) Notice: Subject to any disclaimer, the term of this patent is extended or adjusted under 35 U.S.C. 154(b) by 228 days.

(21) Appl. No.: 16/165,913

(22) Filed: Oct. 19, 2018

(65) Prior Publication Data

US 2019/0053946 A1    Feb. 21, 2019

Related U.S. Application Data

(62) Division of application No. 11/272,571, filed on Nov. 9, 2005, now abandoned.

(51) Int. Cl.
*A61F 9/008* (2006.01)
*G02B 26/08* (2006.01)
(Continued)

(52) U.S. Cl.
CPC .......... *A61F 9/008* (2013.01); *G02B 26/0875* (2013.01); *G02B 26/101* (2013.01); *A61F 9/009* (2013.01); *A61F 2009/00844* (2013.01); *A61F 2009/00872* (2013.01); *A61F 2009/00897* (2013.01)

(58) Field of Classification Search
CPC ...................... A61F 9/008; A61F 9/009; A61F 2009/00844; A61F 2009/00872; A61F 2009/00897; G02B 26/0875; G02B 26/101
See application file for complete search history.

(56) References Cited

U.S. PATENT DOCUMENTS 3,848,104 A    11/1974 Locke
4,002,899 A    1/1977 Stauffer
(Continued)

FOREIGN PATENT DOCUMENTS

EP    1731120 A1    12/2006

OTHER PUBLICATIONS

European Search Report for Application No. EP12194291.6, dated Mar. 15, 2013, 6 pages.
(Continued)

*Primary Examiner* — Catherine M Voorhees
(74) *Attorney, Agent, or Firm* — Johnson & Johnson Surgical Vision, Inc.

(57) ABSTRACT

A laser scanner is disclosed. The laser scanner comprises a laser source, a first optical element, and a focusing element. The first optical element is adapted to move along the optical axis of light from the laser source. The focusing element receives laser light from the first optical element and is adapted to move orthogonally to the optical axis. Optionally, the focusing element may include multiple focusing lenses. A first focusing lens may be adapted to move along a first axis which is orthogonal to the optical axis. A second focusing lens may be adapted to move along a second axis which is orthogonal to the optical axis and to the first axis. The laser scanner may also include a second optical element which receives light from the focusing element and is adapted to effectively increase the focal length of the focusing element without increasing its f number.

21 Claims, 5 Drawing Sheets

(51) Int. Cl.
*G02B 26/10* (2006.01)
*A61F 9/009* (2006.01)

(56) References Cited

U.S. PATENT DOCUMENTS

| | | | |
|---|---|---|---|
| 4,450,358 A | 5/1984 | Reynolds | |
| 4,514,048 A * | 4/1985 | Rogers | G02B 3/14 |
| | | | 351/159.41 |
| 4,538,608 A | 9/1985 | L'Esperance, Jr. | |
| 4,700,056 A | 10/1987 | Silvy et al. | |
| 4,786,124 A | 11/1988 | Stone et al. | |
| 4,899,327 A | 2/1990 | Bates et al. | |
| 4,935,763 A | 6/1990 | Itoh et al. | |
| 4,984,000 A | 1/1991 | Watanabe et al. | |
| 5,098,426 A | 3/1992 | Sklar et al. | |
| 5,161,165 A | 11/1992 | Zorabedian | |
| 5,247,153 A | 9/1993 | Pasch | |
| 5,475,209 A | 12/1995 | Nabeshima | |
| 5,550,367 A * | 8/1996 | Plesko | G02B 3/14 |
| | | | 235/455 |
| 5,634,920 A * | 6/1997 | Hohla | A61F 9/008 |
| | | | 606/10 |
| 5,696,589 A | 12/1997 | Bernacki | |
| 5,720,894 A | 2/1998 | Neev et al. | |
| 5,768,226 A | 6/1998 | Ogino | |
| 5,827,264 A | 10/1998 | Hohla | |
| 5,923,473 A | 7/1999 | Kelley et al. | |
| 5,993,438 A | 11/1999 | Juhasz et al. | |
| 6,011,643 A * | 1/2000 | Wunderlich | G02B 26/101 |
| | | | 348/746 |
| 6,043,843 A * | 3/2000 | Kelley | G02B 26/00 |
| | | | 348/207.99 |
| 6,110,166 A | 8/2000 | Juhasz | |
| 6,146,375 A | 11/2000 | Juhasz et al. | |
| 6,160,910 A | 12/2000 | Freifeld | |
| 6,254,595 B1 | 7/2001 | Juhasz et al. | |
| 6,304,359 B1 | 10/2001 | Gadhok | |
| 6,325,793 B1 | 12/2001 | Tomita | |
| 6,462,814 B1 | 10/2002 | Lo | |
| 6,483,071 B1 | 11/2002 | Hunter et al. | |
| 2002/0156486 A1 | 10/2002 | Nadel | |
| 2002/0158131 A1 * | 10/2002 | Dickson | G02B 26/106 |
| | | | 235/462.34 |
| 2003/0212387 A1 | 11/2003 | Kurtz et al. | |
| 2004/0021874 A1 | 2/2004 | Shimmick | |
| 2004/0147913 A1 | 7/2004 | Sinofsky | |
| 2004/0170312 A1 | 9/2004 | Soenksen | |
| 2005/0143719 A1 | 6/2005 | Sink | |
| 2005/0228366 A1 | 10/2005 | Kessler et al. | |

OTHER PUBLICATIONS

Examiner's Communication for Application No. EP06827650, dated Jul. 3, 2012, 4 pages.
Examiner's Communication for Application No. EP06827650, dated Feb. 6, 2012, 3 pages.
Examiner's First Report dated Sep. 15, 2011 for Australian Application No. 2006311513 filed Nov. 8, 2006.
International Preliminary Report on Patentability and Written Opinion for Application No. PCT/US2006/43562, dated Apr. 22, 2009, 4 pages.
International Search Report for Application No. PCT/US2006/43562, dated Jul. 7, 2008, 1 page.
Office Action dated May 30, 2012 for Taiwanese Application No. 095141392, 17 pages.
Supplementary European Search Report for Application No. EP06827650, dated May 18, 2011, 5 pages.

* cited by examiner

LASER SCANNER

This application is a divisional application under 35 USC § 121 of U.S. patent application Ser. No. 11/272,571, filed Nov. 9, 2005, now pending, the entire disclosure of which is incorporated herein by reference.

BACKGROUND OF THE INVENTION

1. Field of the Invention

The field of the present invention is laser scanners, particularly laser scanners that may be employed for ophthalmic laser surgery.

2. Background

Laser scanners for ophthalmic laser surgery generally utilize a pair of scanning mirrors to angularly deflect and scan the laser beam. Typically two scanning mirrors are employed, each scanning the laser along one of two orthogonal axes. A focusing objective, whether one lens or several lenses, images the laser beam onto a focal plane of the optical system. The focal point of the laser beam is thus scanned in two dimensions (x and y) within the focal plane of the optical system. Scanning along the third dimension, i.e., moving the focal plane along the optical axis (z-axis), may be achieved by moving the focusing objective, or one or more lenses within the focusing objective, along the optical axis.

The optical systems used to focus ophthalmic surgical lasers are generally quite complex. Such optical systems are typically required to have diffraction limited performance with a high numerical aperture (NA) and to scan the laser beam over an extended range. The moving mirrors that are typically used in such systems create significant design constraints because significantly high field angles are used during the scanning process, thus requiring optical correction for aberrations such as astigmatism, coma, and other higher order aberrations. In addition, since the beam is scanned angularly, off-axis aberrations of the objective are typically generated and require correction.

The optics required to correct the aberrations created in such laser scanners of the prior art tend to add to the weight and cost of the overall optical system. The overall cost added to such systems may be in the range of tens of thousands of dollars or more. The overall weight of laser scanners, with corrected optics, can be in the range of five kilograms or more. Such heavy systems are extremely difficult to manually position over a patient's eye. To compensate, motorized gantries are frequently employed to move the optics into position with the eye in a "docking" procedure. To assure patient safety during "docking", and to prevent inadvertent movement of the motorized gantry, special safety electronics are included as part of such scanning systems. These additional electronics further increase the complexity and cost of the scanning system.

SUMMARY OF THE INVENTION

The present invention is directed towards a laser scanner. The laser scanner comprises a laser source and optics for scanning the focal point in three dimensions. The optics include optical elements for scanning the laser beam along three orthogonal axes and an optical element which extends the focal plane of the optics away from the focusing lens(es).

In a first separate aspect of the invention, a first optical element and a focusing element are included as part of the optics of the laser scanner. This first optical element is adapted to move along an optical axis of light from the laser source. The focusing element is adapted to move orthogonally to the optical axis. The focal plane depth of the optics may be adjusted through movement the first optical element. Further, the focusing element may include two focusing lenses, each adapted to move along two orthogonal axes, these axes also being orthogonal to the optical axis.

In a second separate aspect of the invention, an optical element within the optics of the laser scanner is adapted to effectively increase the focal length of an included focusing element without increasing the f number of the focusing element. Preferably, the refractive index of this optical element is greater than one.

In a third separate aspect of the invention, the laser scanner is incorporated into a system adapted for ophthalmic laser surgery and includes a mirror optically disposed between the focusing element and the eye on which the surgical procedure is conducted. This mirror is adapted to pass light from the laser source and to reflect visible light. The surgical system also includes a view port optically coupled to the mirror to receive the reflected visible light from the mirror. This view port optionally allows an attending surgeon to directly view the ophthalmic surgical laser procedure as it occurs. If desired, magnification optics may be included as part of the view port to facilitate viewing of the surgical procedure.

In a fourth separate aspect of the invention, the focal point of the laser is scanned in a manner which helps minimize the time needed to scan an entire area. The focal point is scanned along substantially linear path. During the scan along the path, an oscillatory motion is introduced to the scan path in a direction which is orthogonal to the path. In larger scan patterns, this technique may be employed for any linear or substantially linear segment of the scan pattern.

In a fifth separate aspect of the invention, any of the foregoing aspects may be employed in combination.

Accordingly, the present invention provides an improved laser scanner. Other objects and advantages will appear hereinafter.

BRIEF DESCRIPTION OF THE DRAWINGS

In the drawings, wherein like reference numerals refer to similar components.

DETAILED DESCRIPTION OF THE PREFERRED EMBODIMENTS

Figure 1:
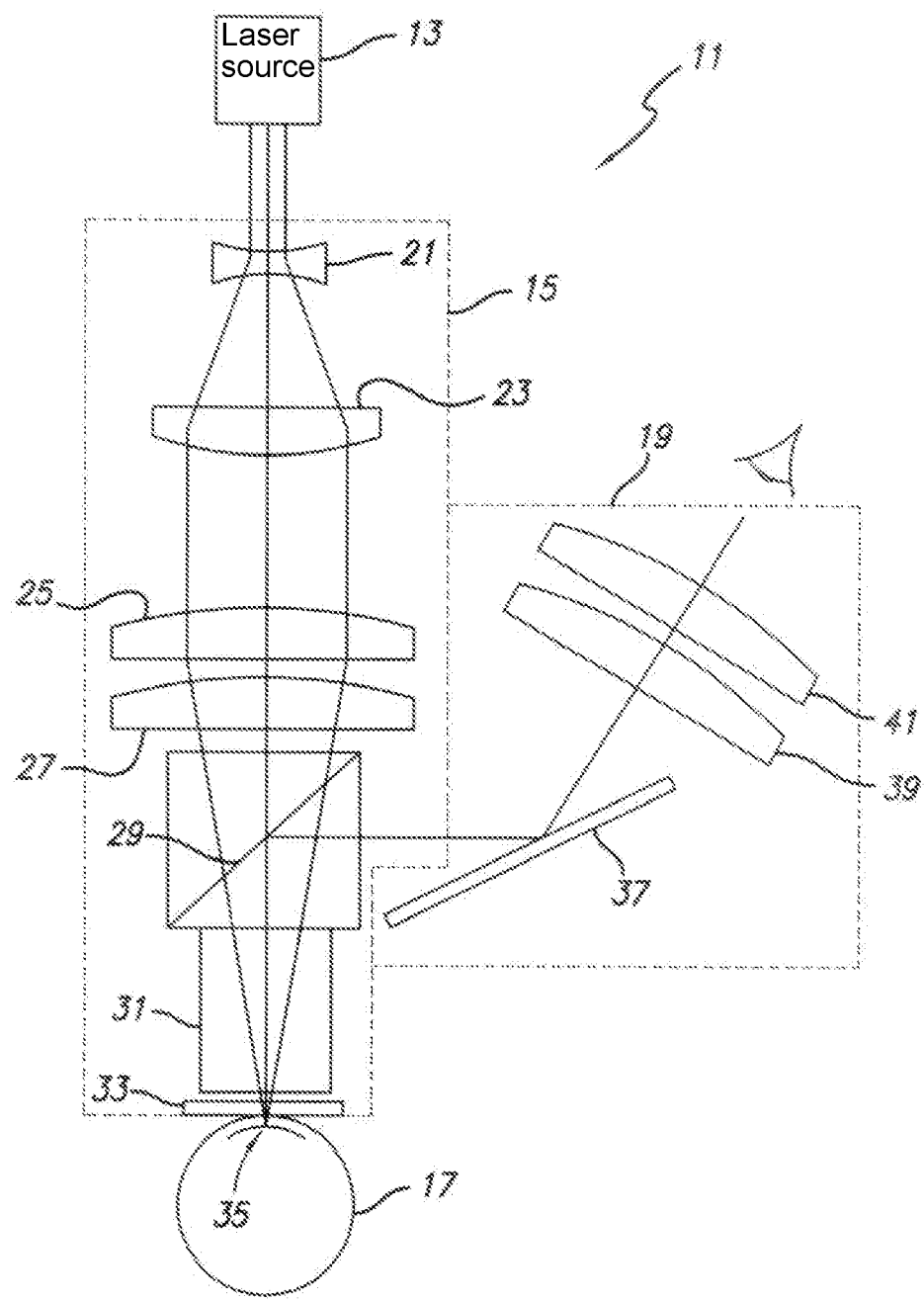
FIG. 1 schematically illustrates a laser scanner.

Turning in detail to the drawings, FIG. 1 illustrates a laser scanner 11 which may advantageously be used for ophthalmic laser surgery. The laser scanner 11 includes a laser source 13 and optics 15 for directing light from the laser source toward an eye 17, along with a view port 19 which enables the physician a view of the eye 17 as surgery proceeds. The laser source 13 may be of any type, but for purposes of ophthalmic laser surgery, the laser source 13 is preferably capable of generating a pulsed laser beam. One such laser source is described in U.S. Pat. No. 4,764,930, the disclosure of which is incorporated herein by reference. Further, the pulsed laser beam preferably has a pulse duration which is as long as a few nanoseconds or as short as a few femtoseconds.

Light emitted from the laser source 13 passes through the movable z-axis scanning lens 21, the collimating lens 23, the two movable focusing lenses 25, 27, the mirror 29, the block of refractive material 31, and the applanation lens 33 to a focal point 35 which is on or within the cornea of the eye 17. Unlike much of the prior art relating to laser scanners, the laser scanner 11 of FIG. 1 does not include any scanning mirrors. As such, light from the laser source is always on-axis as it passes through each optical element. Having an on-axis laser beam greatly reduces or eliminates the need to correct off-axis aberrations, astigmatism, and coma. Elimination of the need for corrective optics in turn reduces the overall weight of the laser scanner, thus making it possible to perform a manual "docking" procedure instead of requiring complex automation to perform the "docking" procedure. This also leads directly to a significant reduction in costs for such laser scanners, and particularly ophthalmic laser surgical equipment which incorporates such laser scanners.

While two focusing lenses 25, 27 are shown, a single movable focusing lens, or alternatively more than two focusing lenses, may be used. Regardless of how many lenses are used as the focusing objective, light from the laser source 13 is preferably focused to less than a 5 μm spot size.

The mirror 29 is transparent to the wavelength of light from the laser source 13, but reflective to light at visible wavelengths. This permits an image of the eye on which a procedure is being performed to be reflected by the mirror 29, toward the view port 19. The view port 19 includes a mirror 37 which directs the image toward magnification lenses 39, 41. Because the mirror 29 extracts the image of the eye 17 at a point between the eye 17 and the objective of the laser scanner optics, the amount of magnification required for the view port 19 is drastically reduced as compared to laser scanner systems of the prior art. While the mirror 29 is shown as a separate optical element from the block of refractive material 31, it may be incorporated into the block of refractive material 31 as a mirrored internal surface or as an interface between two pieces of refractive material, which together form the block of refractive material.

The block of refractive material 31 is included after the focusing objective of the laser scanner optics, i.e., the focusing lenses 25, 27, to effectively extend the focal length of the focusing lenses 25, 27. This is accomplished by using a block of refractive material with a refractive index which is greater than the refractive index of air. With the block of refractive material 31 in place, the actual focal length of the combined focusing lenses can be made relatively short, say on the order of 20 mm, without actually increasing the f number of the focusing lenses. By having focusing lenses with short focal lengths, the need to correct chromatic aberrations, which often arise from focusing optics with long focal lengths, is greatly reduced or eliminated. The effective focal length of the focusing lenses 25, 27, with the refractive material 31 in place, can be significantly lengthened. This facilitates focusing light from the surgical laser on or in the patient's eye from the end of the scanner.

The applanation lens 33 is included to facilitate use of the laser scanner 11 as part of a ophthalmic laser surgery system. The function of the applanation lens 33 is described in U.S. Pat. No. 5,549,632, the disclosure of which is incorporated herein by reference. Other than as a basic block of refractive material disposed between the laser source 13 and the eye 17, the applanation lens 33 is not actively employed in to scan light from the laser across or within the cornea.

Figure 2:
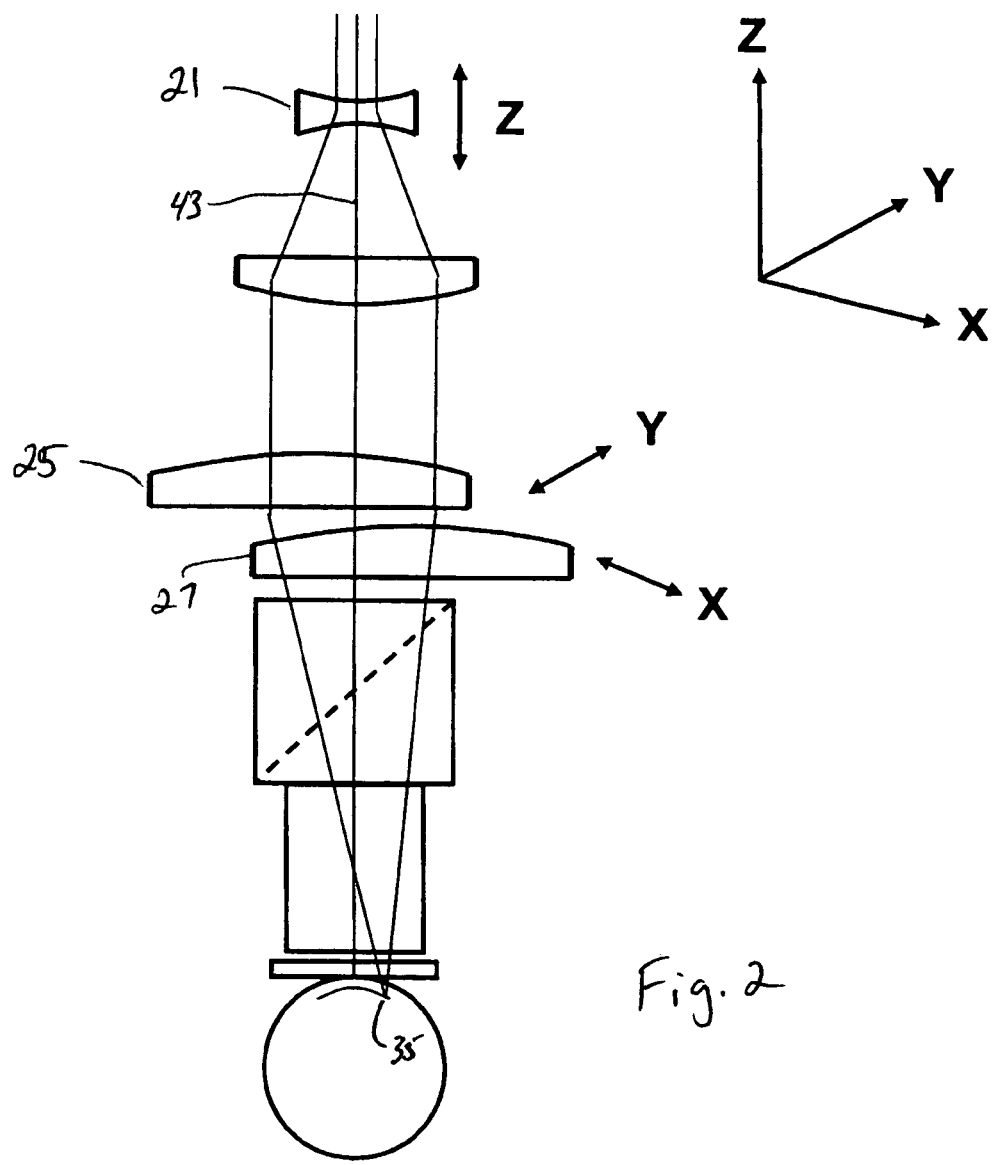
FIG. 2 illustrates the laser scanner of FIG. 1 and how movement of various optical elements enable scanning of the focal point in three dimensions.

Turning to FIG. 2, the z-axis scanning lens 21 is movable along the optical axis 43 of the laser beam. Movement of this z-axis scanning lens 21 may be achieved by a drive mechanism (not shown), which may be of any type known to those skilled in the art, including galvanometers, stepper motors, rotational motors with lead-screw driven linear stages, linear motors, voice coil type linear actuators, piezo actuators, ultrasonic piezo ceramic motors, DC servo motors, and the like. The drive mechanism also preferably includes a feedback loop so that associated control electronics (not shown) can determine the position of the z-axis scanning lens 21 and control the movement thereof. By placing control of the z-axis scanning in a lens which is optically disposed outside of and before the focusing objective, finer control of the z-axis position of the focal point 35 is possible. In the prior art, the z-axis position of the focal point is typically controlled by z-axis movement of the focusing objective itself, giving rise to a 1:1 ratio between movement of the focusing objective and movement of the focal point. In contrast, using the configuration disclosed herein, ratios of 10:1, 100:1, 1000:1, or greater are possible.

Similarly, the first focusing lens 25 is moveable along the y-axis, and the second focusing lens 27 is movable along the x-axis. Movement of these two lenses may be accomplished and controlled in the same manner as movement and control of the z-axis scanning lens 21. Movement of each of these two focusing lenses 25, 27 along their respective axes results in scanning of the focal point 35 along those axes within the focal plane. Each of the focusing lenses 25, 27 are shown displaced along the x- and y-axes in FIG. 2, resulting in the focal point 35 being scanned to an off-axis position within the focal plane. In the event that a single focusing lens is employed, the single lens would be movable within the plane defined by the x- and y-axes, thereby permitting the focal point to be scanned across the entire focal plane.

Use of the described laser scanner within an ophthalmic laser surgery system and in conjunction with a computer to control the position and motion of the z-axis scanning lens and the two focusing lenses, permits fine control over the laser scanner so that the scannable focal point may be used to create surgical cuts on or within the cornea of the eye.

Figure 3:
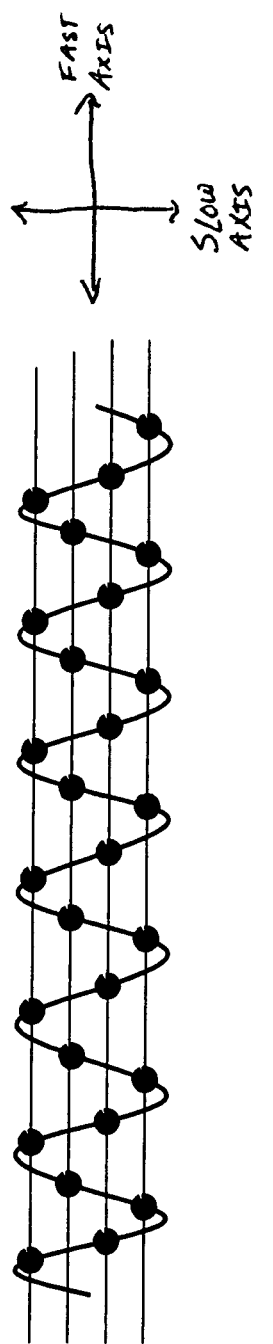
FIG. 3 illustrates a first focal point scan pattern which may be advantageously realized using the laser scanner of FIG. 1.

FIG. 3 illustrates a scan pattern which includes linear motion along one axis (the "fast axis") and small amplitude, high frequency oscillations along the second, orthogonal axis (the "slow axis"). This type of scan pattern may be employed to effectively increase the coverage area of the laser scanner without requiring an increase in scan speed along the fast axis. Moreover, it may be employed during any essentially linear motion of the laser scanner, regardless of the actual scan direction. For a given linear speed, the effective coverage area is increased by approximately four times. The oscillatory motion along the slow axis may be achieved through the scanner motor(s) which drive the x-axis and/or y-axis scanning lens(es), or alternatively, it may be achieved by additional scanner motor(s) which superimpose the oscillatory motion on onto the linear motion of the scanning lens(es).

Figure 4:
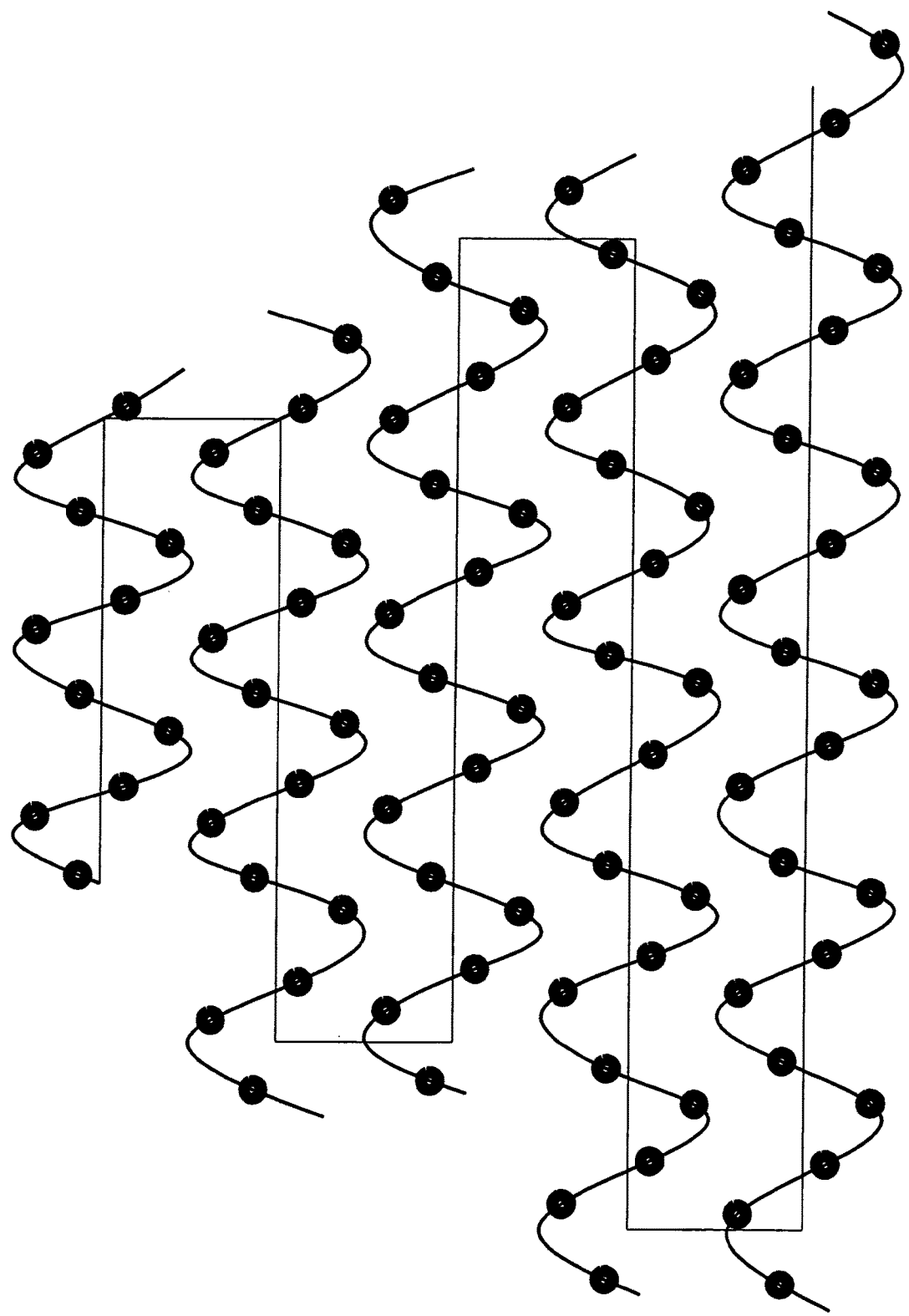
FIG. 4 illustrates a second focal point scan pattern which may be advantageously realized using the laser scanner of FIG. 1.
Figure 5:
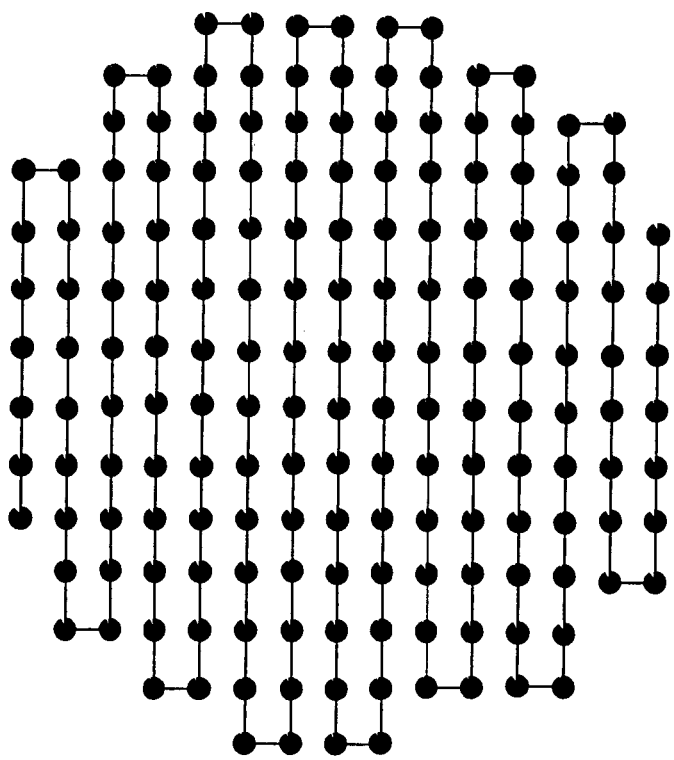
FIG. 5 illustrates a raster scan in accordance with the prior art.

FIG. 4 shows how the oscillatory motion described above may be advantageously employed to increase the effective coverage area for each linear pass along the fast axis as compared to a common raster pattern, which is illustrated in FIG. 5. By reducing the number of passes necessary to scan the same area, the time needed to scan an entire area may be significantly reduced.

Thus, an improved laser scanner is disclosed. While embodiments of this invention have been shown and described, it will be apparent to those skilled in the art that many more modifications are possible without departing from the inventive concepts herein. Particularly, light from the laser source is shown passing directly from one optical element to the next. The particular configuration of mirrors and lenses described herein, however, is merely illustrative of the optics underlying the laser scanner. Alternative embodiments, which may include additional or different optical elements to accommodate a desired mechanical or optical configuration, are possible. The invention, therefore, is not to be restricted except in the spirit of the following claims.

What is claimed is:

1. A laser scanner comprising:
   a laser source;
   a first optical element adapted to move along an optical axis of light from the laser source;
   a focusing element receiving laser light from the first optical element, wherein the focusing element is adapted to move orthogonally to the optical axis; and
   a second optical element, which is a block of refractive material having a refractive index greater than one, the second optical element receiving laser light from the focusing element on a first flat surface at a first side of the second optical element and transmitting the laser light out of a second flat surface at a second side of the second optical element which is different from the first side, wherein the second optical element is adapted to effectively increase a focal length of the focusing element without increasing the f number of the focusing element.

2. The laser scanner of claim 1 further comprising a collimating lens optically disposed between the first optical element and the focusing element.

3. The laser scanner of claim 1, wherein the focusing element comprises a first focusing lens adapted to move along a first axis, the first axis being orthogonal to the optical axis.

4. The laser scanner of claim 3, wherein the focusing element further comprises a second focusing lens adapted to move along a second axis, the second axis being orthogonal to the first axis and to the optical axis.

5. The laser scanner of claim 1 further comprising a mirror optically disposed between the focusing element and the second optical element, the mirror being adapted to pass light from the laser source and to reflect visible light.

6. The laser scanner claim 1,
   wherein the first optical element is a scanning lens; and
   wherein the focusing element includes first and second focusing lenses, wherein the first focusing lens is adapted to move along a first axis, the first axis being orthogonal to the optical axis, and the second focusing lens is adapted to move along a second axis, the second axis being orthogonal to the first axis and to the optical axis.

7. The laser scanner of claim 6, further comprising:
   a collimating lens disposed between the scanning lens and the first and second focusing lenses; and
   a mirror optically disposed between the focusing element and the block of refractive material, the mirror being adapted to pass light from the laser source and to reflect visible light.

8. A method of scanning light from a laser source, the method comprising
   directing light from the laser source through an optical system to a focal point, the optical system comprising, in optical alignment, a scanning lens, a focusing element, and an optical element, wherein the optical element is a block of refractive material having a refractive index greater than one and receives the light on a first flat surface at a first side of the optical element and transmits the light out of a second flat surface at a second side of the optical element which is different from the first side and is adapted to effectively increase a focal length of the focusing element without increasing the f number of the focusing element;
   moving the scanning lens along a z-axis to adjust a depth of the focal point along the z-axis; and
   moving the focusing element in a plane orthogonal to the z-axis to adjust a position of the focal point relative to the z-axis.

9. The method of claim 8, wherein the focusing element comprises first and second focusing lenses.

10. The method of claim 9, wherein moving the focusing element includes moving the first focusing lens along a first axis, the first axis being orthogonal to the z-axis.

11. The method of claim 10, wherein moving the focusing element includes moving the second focusing lens along a second axis, the second axis being orthogonal to the z-axis and to the first axis.

12. The method of claim 8,
    wherein the optical system further comprises a collimating lens, wherein the focusing element includes first and second focusing lenses, and
    wherein the step of moving the focusing element includes:
    moving the first focusing lens along a first axis to adjust a position of the focal point relative to the z-axis, the first axis being orthogonal to the z-axis; and
    moving the second focusing lens along a second axis to further adjust a position of the focal point relative to the z-axis, the second axis being orthogonal to the z-axis and to the first axis.

13. The laser scanner of claim 1, further comprising:
    a mirror optically disposed between the focusing element and the second optical element, the mirror being adapted to pass light from the laser source and to reflect visible light; and
    a view port optically coupled to the mirror to receive the reflected visible light.

14. The system of claim 13, wherein the first optical element, the focusing element and the second optical element are adapted to direct light from the laser source toward an eye, and wherein the mirror is adapted to reflect an image of the eye.

15. The system of claim 13, wherein the view port comprises one or more magnifying lenses.

16. A laser scanner comprising:
    a laser source adapted to emit laser light along an optical axis;
    a first optical element disposed downstream of the laser source and receiving the laser light from the laser source, wherein the first optical element is adapted to move along the optical axis;
    a focusing element disposed downstream of the first optical element and receiving laser light from the first optical element, wherein the focusing element has an associated focal point and is adapted to move orthogonally to the optical axis; and a second optical element, which is a block of refractive material having a refractive index greater than one, the second optical element being disposed downstream of the focusing element and receiving laser light from the focusing element on a first flat surface at a first side of the second optical element and transmitting the laser light out of a second flat surface at a second side of the second optical element which is different from the first side, wherein the second optical element causes the laser light from the focusing element to focus to a point downstream of the focal point associated with the focusing element without increasing the f number of the focusing element.

17. The laser scanner of claim 16, wherein the focusing element comprises a first focusing lens adapted to move along a first axis orthogonal to the optical axis.

18. The laser scanner of claim 17, wherein the focusing element further comprises a second focusing lens adapted to move along a second axis orthogonal to the first axis and the optical axis.

19. A method of scanning light from a laser source, the method comprising:

directing laser light from the laser source along an optical axis of an optical system and through a scanning lens and a focusing element of the optical system, the focusing element having an associated focal point;

refracting the laser light from the focusing element with an optical element of the optical system, the optical element being a block of refractive material having a refractive index greater than one and receiving the laser light on a first flat surface at a first side of the optical element and transmitting the light out of a second flat surface at a second side of the optical element which is different from the first side, to focus the laser light from the focusing element onto a focusing point downstream of the focal point associated with the focusing element without increasing the f number of the focusing element;

moving the scanning lens along the optical axis to adjust a depth of the focal point along the optical axis; and moving the focusing element in a plane orthogonal to the optical axis to adjust a position of the focusing point relative to the optical axis.

20. The method of claim 19, wherein the focusing element comprises a first focusing lens and moving the focusing element in a plane orthogonal to the optical axis comprises moving the first focusing lens along a first axis orthogonal to the optical axis.

21. The method of claim 20, wherein the focusing element further comprises a second focusing lens and moving the focusing element in a plane orthogonal to the optical axis comprises moving the second focusing lens along a second axis orthogonal to the optical axis.

* * * * *